(12) United States Patent
Donnelly et al.

(10) Patent No.: US 8,529,452 B2
(45) Date of Patent: Sep. 10, 2013

(54) ULTRASONIC EVALUATION OF VENOUS STRUCTURES

(76) Inventors: Sandra Donnelly, Mississauga (CA); Derek Muradali, Toronto (CA)

(*) Notice: Subject to any disclaimer, the term of this patent is extended or adjusted under 35 U.S.C. 154(b) by 436 days.

(21) Appl. No.: 12/303,137

(22) PCT Filed: Jun. 1, 2007

(86) PCT No.: PCT/CA2007/000986
§ 371 (c)(1),
(2), (4) Date: Jan. 28, 2010

(87) PCT Pub. No.: WO2007/140593
PCT Pub. Date: Dec. 13, 2007

(65) Prior Publication Data
US 2010/0130864 A1    May 27, 2010

Related U.S. Application Data

(60) Provisional application No. 60/810,246, filed on Jun. 2, 2006.

(51) Int. Cl.
*A61B 8/00* (2006.01)
(52) U.S. Cl.
USPC ............ 600/449; 600/407; 600/437; 600/443
(58) Field of Classification Search
USPC ................. 600/407, 437, 449, 454, 467–468, 600/479–485; 382/128
See application file for complete search history.

(56) References Cited

U.S. PATENT DOCUMENTS

| 7,255,678 | B2 | 8/2007 | Mehi et al. | |
|---|---|---|---|---|
| 2003/0097040 | A1* | 5/2003 | Clerin et al. | 600/36 |
| 2005/0124892 | A1* | 6/2005 | Weitzel et al. | 600/449 |
| 2008/0119879 | A1* | 5/2008 | Brenneman et al. | 606/153 |
| 2008/0119946 | A1* | 5/2008 | Nugent et al. | 623/23.72 |

FOREIGN PATENT DOCUMENTS

| EP | 1693005 A | 8/2006 |
|---|---|---|
| EP | 2029025 B1 | 3/2011 |
| FR | 2853519 A | 10/2004 |
| WO | WO-2005055831 A1 | 6/2005 |
| WO | WO-2007056104 A3 | 8/2007 |
| WO | WO-2007140593 | 12/2007 |

OTHER PUBLICATIONS

European Patent Office, Extended European Search Report, EP Patent Application 07719902.4, mailed Nov. 10, 2009, 7 pages.
Grogan, J. et al. "Frequency of critical stenosis in primary arteriovenous fistulae before hemodialysis access: Should duplex ultrasound surveillance be the standard of care?" *Journal of Vascular Surgery*, vol. 41, No. 6, Jun. 1, 2005, pp. 1000-1006.

(Continued)

*Primary Examiner* — Tse Chen
*Assistant Examiner* — Joel F Brutus
(74) *Attorney, Agent, or Firm* — Perkins Coie LLP

(57) ABSTRACT

Provided are methods and systems for detecting a maturing arterio-venous fistula comprising a vein. An exemplary method comprises determining a wall thickness of the fistula and a lumen diameter of the fistula vein using a high frequency ultrasound imaging system. A blood pressure of the subject is determined. A circumferential vessel wall stress is determined from the measured blood pressure, the wall thickness of the fistula and a determined radius of the measured diameter of the fistula. The determined circumferential vessel stress is compared to a predetermined threshold stress to determine if the fistula is mature.

18 Claims, 7 Drawing Sheets

(56) References Cited

OTHER PUBLICATIONS

Pietura, R. et al. "Colour Doppler ultrasound assessment of well-functioning mature arteriovenous fistulas for haemodialysis access." *European Journal of Radiology*, vol. 55, No. 1, Jul. 1, 20,05, pp. 113-119.

Oates, C.P. et al. "The use of a diasonics DRF400 duplex ultrasound scanner to measure volume flow in arterio-venous fistulae in patients undergoing haemodialysis: An analysis of measurement uncertainties." *Ultrasound in Medicine and Biology*, vol. 16, No. 6, Jan. 1, 1009, pp. 571-579.

International Searching Authority, International Search Report, PCT Application PCT/CA2007/000986, mailed Sep. 20, 2007, 2 pages.

Robbin, M.L. et al. "Hemodialysis arteriovenous fistula maturity: US evaluation." *Radiology*, vol. 225, No. 1, Oct. 2002, pp. 59-64.

Patel, Sheela T. et al. "Failure of arteriovenous fistula maturation: An unintended consequence of exceeding Dialysis Outcome Quality Initative guidelines for hemodialysis access," *Journal of Vascular Surgery*, vol. 38, No. 3, Sep. 2003, pp. 439-445.

Malovrh, M. "The Role of Sonography in the Planning of Arteriovenous Fistulas for Hemodialysis," *Seminars in Dialysis*, vol. 16, No. 4, Jul. 2003-Aug. 2003, pp. 299-303.

International Searching Authority, Written Opinion, PCT Application PCT/CA2007/000986, mailed Sep. 20, 2007, 6 pages.

\* cited by examiner

ULTRASONIC EVALUATION OF VENOUS STRUCTURES

CROSS-REFERENCE TO RELATED APPLICATIONS

This application is the National Stage of International Application No. PCT/CA2007/000986, filed Jun. 1, 2007, which claims the benefit of U.S. Provisional Application No. 60/810,246 filed Jun. 2, 2006, which is incorporated herein by reference in its entirety.

BACKGROUND OF THE INVENTION

The need for access to the circulation is paramount for delivery of renal replacement therapy (RRT) by hemodialysis. The use of a native arterio-venous (AV) fistula provides access with the fewest complications of thrombosis, infection and hospitalization. The creation of the AV fistula is followed by a maturing time in which vascular remodeling occurs. The natural history of this process is not well defined. Moreover, the current challenges of vascular access are expected to increase over time as the typical incident patients are older and have more co-morbid vascular and metabolic disease.

SUMMARY OF THE INVENTION

Provided are methods and systems for detecting a maturing or mature arterio-venous fistula comprising a vein. Also provided are methods and systems for detecting the thickening of a vein wall.

Other apparatus, methods, aspects and advantages of the invention will be discussed with reference to the Figures and to the detailed description of the preferred embodiments.

BRIEF DESCRIPTION OF THE FIGURES

The accompanying drawings, which are incorporated in and constitute a part of this specification, illustrate several aspects described below and together with the description, serve to explain the principles of the invention.

DETAILED DESCRIPTION OF THE INVENTION

Figure 1:
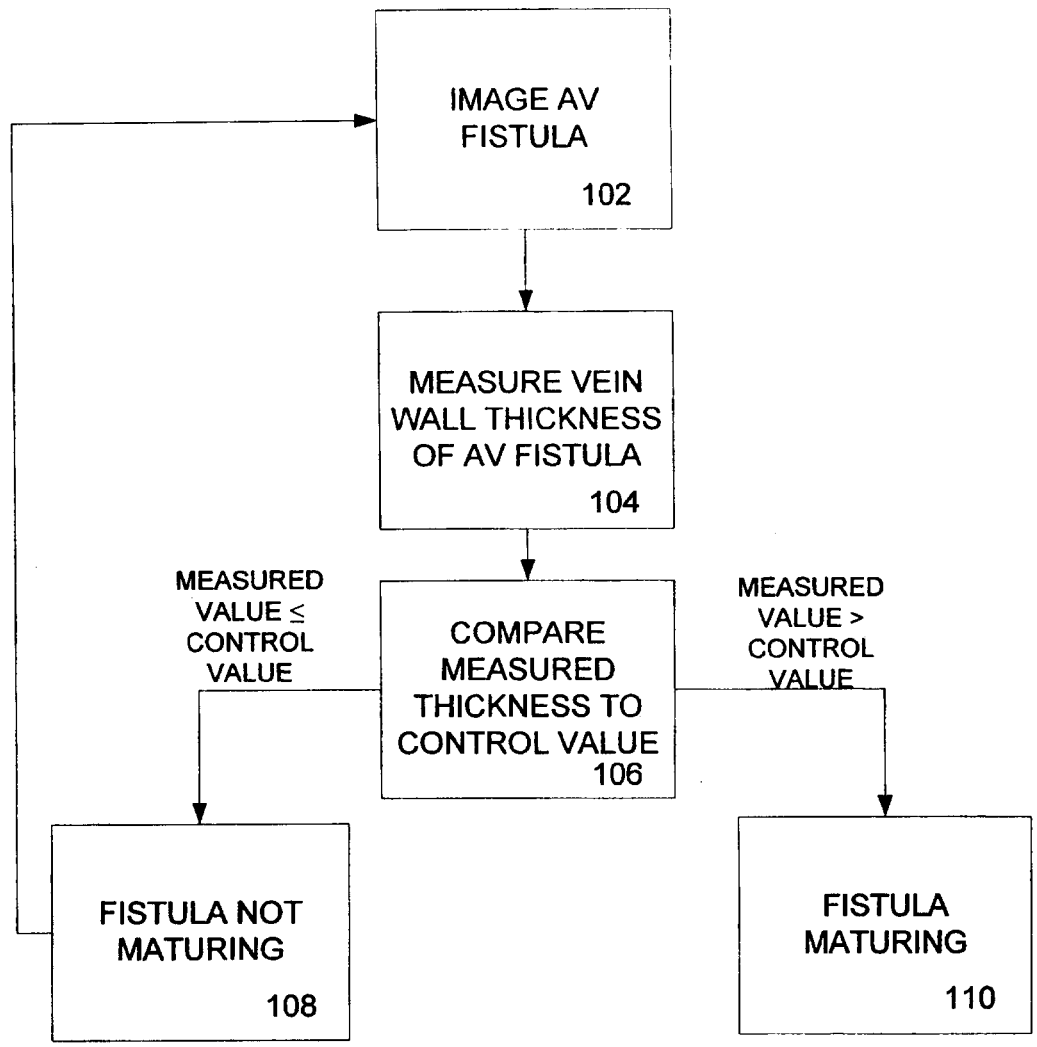
FIG. 1 is a block flow diagram illustrating an exemplary method of detecting a maturing AV fistula in a subject.

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a respiration waveform" can include two or more such waveforms unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The present invention may be understood more readily by reference to the following detailed description of preferred embodiments of the invention and the examples included therein and to the Figures and their previous and following description.

By a "subject" is meant an individual. The term subject includes small or laboratory animals as well as primates, including humans. A laboratory animal includes, but is not limited to, a rodent such as a mouse or a rat. The term laboratory animal is also used interchangeably with animal, small animal, small laboratory animal, or subject, which includes mice, rats, cats, dogs, fish, rabbits, guinea pigs, rodents, etc. The term laboratory animal does not denote a particular age or sex. Thus, adult and newborn animals, as well as fetuses (including embryos), whether male or female, are included. The term "patient" includes human and veterinary patients.

The use of veins for the repeated puncture necessary to perform hemodialysis on a patient requires vascular remodeling such that the vessel dilates and the walls, particularly the muscular media, undergo hypertrophy. A remodeled vein then provides the blood flow required to support dialysis and the vessel integrity to withstand repeated cannulation and hemodialysis. At this point the fistula is deemed to have "matured." Thus, an arterio-venous fistula comprises a vein that has undergone a maturation process.

The methods described herein can be used to monitor the maturation of a fistula and to determine when the fistula is mature. The methods can utilize high frequency ultrasound to analyze anatomical features of a fistula to determine if it is maturing or mature. For example, non-limiting features that can be monitored or analyzed include, vein wall thickness, vein lumen diameter, blood flow velocity, blood pressure, and wall thickness consistency. These features can be used alone or in combination to determine whether a fistula is maturing or is mature. For various exemplary aspects, the pressure, diameter of the vessel, and the wall thickness can be used to determine the wall tension.

In one aspect, the systems, methods and apparatuses can track the maturation of an AV fistula using a high frequency ultrasound imaging system. As used herein, high frequency ultrasound refers to ultrasound of a sufficiently high frequency to accurately resolve vein wall thickness. In some aspects, such systems can transmit ultrasound at a center transducer frequency of 20 MHz or higher. A high frequency ultrasound probe can be used to image the blood vessels. In a further aspect, the natural history of effective maturation of the fistula can be evaluated and the parameters that define readiness for successful cannulation can be determined.

Provided herein are methods and systems for detecting a maturing arterio-venous fistula comprising a vein. An exemplary method comprises determining an initial wall thickness of the vein using a high frequency ultrasound imaging system. A subsequent wall thickness can be determined by using a high frequency ultrasound imaging system. The initial wall thickness can be compared to a subsequent wall thickness. When compared, an increase in the subsequent wall thickness compared to the initial wall thickness indicates a maturing arterio-venous fistula.

In the described methods, if the vein is part of an arteriovenous fistula, a thickened wall vein can indicate a maturing and/or a mature fistula. Therefore, comparing an initial wall thickness to a subsequent wall thickness can be used to indicate a maturing or mature arterio-venous fistula. One skilled in the art will appreciate that, for example, an increase in the subsequent wall thickness compared to the initial wall thickness can indicate a mature arterio-venous fistula or can indicate a maturing fistula.

In one aspect, the vein wall thickness can be determined using a high frequency ultrasound system. For example, the determination of an initial and subsequent wall thickness can comprise producing an ultrasonic image of the vein using the high frequency ultrasound system. In exemplary aspects, a longitudinal B-mode image can be taken along the vein or a portion thereof. Optionally, the ultrasonic image can also be a horizontal B-scan image showing a cross-section of the vein. In another aspect, one or more longitudinal or horizontal B-scan images can be taken of the vein.

Optionally, longitudinal B-scan image slices are taken from multiple angles. For example, an image can be taken from the left side of the vein or fistula and an image can be taken from the right side of the fistula. If horizontal images are taken, multiple B-mode slices can be taken along the length of the vein or fistula. The thickness of the vein wall can be measured at one or more location. Thus, if multiple horizontal image slices are taken, the thickness of the vein wall can be measured at one or more location in one or more image slice. Similarly, if one or more longitudinal B-mode slice is taken, then the vein wall thickness can be determined at one or more location in one or more image slice. In the case of a longitudinal image, the superficial wall of the vein can be designated the near wall and the deep wall can be designated the far wall. In a further aspect, measurement of vein thickness can comprise measurements of the thickness of the near and far wall.

In operation, ultrasound images are normally formed by the analysis and amalgamation of multiple pulse echo events. An image is formed, effectively, by scanning regions within a desired imaging area using individual pulse echo events, referred to as "A-Scans" or ultrasound "lines." Each pulse echo event requires a minimum time for the acoustic energy to propagate into the subject and to return to the transducer. An image is completed by "covering" the desired image area with a sufficient number of scan lines, referred to as "painting in" the desired imaging area so that sufficient detail of the subject anatomy can be displayed. The number of and order in which the lines are acquired can be controlled by the ultrasound system, which also converts the raw data acquired into an image. Using a combination of hardware electronics and software instructions in a process called "scan conversion," or image construction, the ultrasound image obtained is rendered so that a user viewing the display can view the subject being imaged.

Ultrasound imaging systems can transmit pulsed energy along a number of different directions, or ultrasonic beams, and thereby receive diagnostic information as a function of both lateral directions across the body and axial distance into the body. This information can be displayed as two dimensional, "B-scan" images. Such a two-dimensional presentation gives a planar view, or "slice" through the body and shows the location and relative orientation of many features and characteristics within the body.

The desired ultrasound for use with the disclosed methods can be applied, transmitted and received using an ultrasonic scanning device that can supply ultrasound at a center frequency sufficient to accurately resolve the thickness of a vein wall. For example, a system with a center frequency transmit of at least about 10 MHz to the highest practical frequency can be used. In exemplary aspects, ultrasound can be supplied at 20 MHz, 25 MHz, 30 MHz, 35 MHz, 40 MHz, 45 MHz, 50 MHz, 55 MHz, 60 MHz, 65 MHz, 70 MHz, or higher. Thus, an ultrasound system or device capable of operating at 20 MHz or above can be used.

One such exemplary system is the VisualSonics™ (Toronto, Calif.) UBM system model VS40 VEVO™ 660. Another exemplary system is the VisualSonics™ (Toronto, Calif.) model VEVO™ 770.

Another such exemplary system can have the components and functionality described in U.S. patent application Ser. No. 10/683,890, US patent application publication 20040122319, which is incorporated herein by reference. Another such exemplary system can have components and functionality described in PCT/US2006/042891, publication number WO2007056104.

It is contemplated that any system capable of producing an ultrasound image using a high frequency ultrasound can be used. Thus, the methods can be practiced using a mechanically scanned ultrasound system that can translate an ultrasound beam as it sweeps along a path. The methods can also be practiced using an array based system where the beam is translated by electrical steering of an ultrasound beam along the elements of the transducer. One skilled in the art will readily appreciate that beams translated from either type system can be used in the described methods, without any limitation to the type of system employed. The type of system is therefore not intended to be a limitation to any described method because array and mechanically scanned systems can be used interchangeably to perform the described methods.

In one aspect, measuring the thickness of the vein wall can comprise identifying the lower surface of the vein tunica adventitia on an ultrasonic image and identifying the interface of the vein tunica intima with the vein lumen. The distance between these two anatomical locations can be measured and the distance between the two can indicate the thickness of the vein wall at that given location. Thus, a location on the image corresponding to the outer wall of the vein and a location corresponding to inner surface of the lumen of the vein can be identified. Optionally, a location of an ultrasound image corresponding to the outer wall of the vein is identified by identifying the lower surface of the vein tunica adventitia on an ultrasound image. A location corresponding to inner surface of the lumen of the vein is optionally identified by identifying the interface of the vein tunica intima with the vein lumen.

In another aspect, portions of the vein wall can also be traced prior to determination of vein wall thickness. For example, the thickness of the vein wall can be measured by tracing at least a portion of the lower surface of the tunica adventitia and at least a portion of the tunica intimia. Once traced, the distance between any two points on the opposed tracings can be determined that indicate the wall thickness. An average distance between the tracings can be determined to indicate an average wall thickness, and/or the area between the traced wall portions can be determined. The selection of any portion on the ultrasound images, the tracing functions, and the measurement functions are common features of ultrasound imaging systems. These features can be automated, semi-automated or can be accomplished by a user of an ultrasound system.

Optionally, a minimal vein wall thickness and a maximal vein wall thickness at the initial and subsequent time can be determined. An initial minimal wall thickness measurement can be compared to a subsequent minimal wall thickness measurement to determine if the wall has thickened, or if a fistula is maturing or mature. In a further aspect, an initial maximal wall thickness measurement can also be compared to a subsequent wall thickness measurement.

It is contemplated that with all the methods of measuring the thickness of one or more vein walls and/or determining the maturity or maturation processes of a fistula, the same general anatomical location of the fistula or vein can be imaged. For example, markings can be placed on the subject's skin or within the subject's tissue indicating where an ultrasound probe should be placed to image the same or same general area of the fistula or vein.

Another exemplary embodiment of a method of detecting a thickened vein wall located in a subject comprises determining a wall thickness of the vein using a high frequency ultrasound imaging system and comparing the determined wall thickness to a control wall thickness value. As one would appreciate, a larger determined wall thickness as compared to the control wall thickness value indicates a thickened vein wall. Further, if the vein is part of a fistula, a determination that the wall is thickened can indicate that the fistula is maturing or that the fistula is mature.

As used herein, "thickening" or "increased thickness" or "maturing fistula" can mean an increase in the thickness of a vein wall as compared to a control value. A control value can be from the same subject or can be from a different subject. Thus, a "control" can comprise either a vein wall thickness measurement obtained from a control subject (e.g., for example and not meant to be limiting, from the same subject before fistula formation, or at a time after fistula formation but prior to the non-control measurement, or from a second subject without a fistula or after fistula formation but at a prior time measured from the date of fistula formation as compared to the time from fistula formation for the non-control measurement) or can comprise a known standard. For example, a standard vein wall thickness can be established for different times subsequent to fistula formation in a subject.

In one aspect, the described methods can detect an increase in wall thickness regardless of the cause of wall thickening. For example, an increase in wall thickness can be correlated with muscular hypertrophy in a vein located in a subject.

One exemplary method for detecting thickened vein wall located in a subject or for monitoring the maturation of a fistula comprising a vein is shown in FIG. 1. The exemplary method 100 comprises creating an image of the vein using a high frequency ultrasound imaging system as shown in block 102. A location on the image corresponding to the outer wall of the vein and a location corresponding to inner surface of the lumen of the vein are identified. The distance between the locations can be determined as shown in block 104. The distance between the locations can correspond to a thickness of the wall of the vein. The determined wall thickness determined can be compared to a control wall thickness value as shown in block 106.

A larger determined wall thickness as compared to the control wall thickness value can indicate a thickened vein wall or maturing fistula as shown in block 110. If the vein wall thickness is equal to or less than the control value, the fistula is determined to not be mature and the process can be repeated as shown in block 108.

Figure 2:
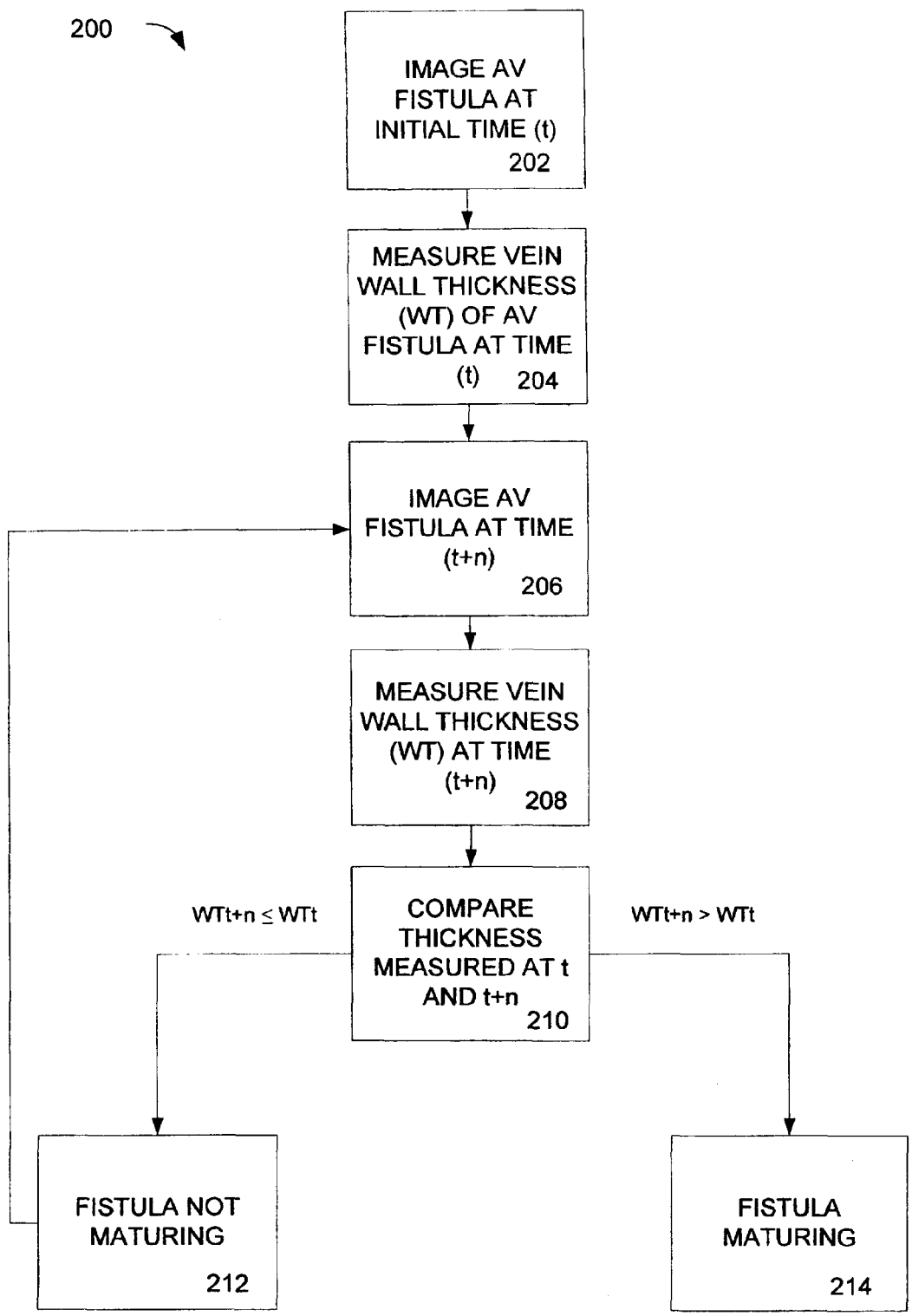
FIG. 2 is a block flow diagram illustrating an exemplary method of detecting a maturing AV fistula in a subject.

Another exemplary method of detecting a thickened vein wall located in a subject or a maturing fistula comprising a vein is shown in FIG. 2. The method can comprise creating a first image at time (t) of the vein using a high frequency ultrasound imaging system as shown in block 202. A location on the first image corresponding to the outer wall of the vein and a location corresponding to inner surface of the lumen of the vein can be identified. The distance between the locations can be determined or measured as shown in block 204. The distance between the locations can correspond to a first thickness of the wall of the vein. A second image of the vein can also be created using a high frequency ultrasound imaging system as shown in block 206 at time (t+n) as shown in block 208. A location on the second image corresponding to the outer wall of the vein and a location corresponding to inner surface of the lumen of the vein can be identified. The distance between the locations identified on the second image can be determined to measure the wall thickness at time (t+n). The distance between the locations on the second image can correspond to a second thickness of the wall of the vein at a subsequent time. The determined first wall thickness can be compared to the determined second wall thickness as shown in block 210. A larger second determined wall thickness as compared to the first determined wall thickness indicates a thickened vein wall or a maturing fistula as shown in block 214. If the wall thickness taken at time (t+n) is equal to or less than the wall thickness at time (t) then the fistula is not maturing as shown in block 212. The process can be repeated by taking a subsequent image and repeating the measurement a comparison steps.

It has been demonstrated that blood vessels typically maintain their original level of wall shear stress. Outflow vein dilatation following AV fistula creation is governed in part by a process of wall shear stress homeostasis. For Poiseuille Flow (steady laminar flow in a cylindrical vessel), wall shear stress τ is given by:

$$\tau = \frac{4\mu Q}{\pi R^3}$$

where μ is viscosity, Q is volumetric flow rate and R is the radius of the vessel. Using this relationship, wall shear stress is directly proportional to volumetric flow rate and inversely related to the third power of the vessel radius. Consequently, if the creation of an arteriovenous fistula increases the volumetric flow in the outflow vein by a factor of X, the radius of the vessel increases generally by a factor of $X^{1/3}$ in order to maintain the same level of wall shear stress. Hoop stress, circumferential vessel wall stress, or stress values are expressed herein in units of Newtons per square meter ($N/m^2$). These terms are used synonymously throughout unless the context dictates otherwise.

The walls of blood vessels are made up of lamellar units, which are circumferentially oriented musculo-elastic fascicles of uniform size that are aligned in the direction of tensile stress. Each lamellar unit supports approximately the same level of tensile stress. Thus, if the tensile stress in the vessel increases, the number of lamellar units increases proportionally. This effectively creates a mechanism which maintains a constant level of intramural stress (intramural stress homeostasis). Thus, by application of Laplace's Law, the circumferential (hoop) stress σ in a cylindrical vessel can be approximated by:

$$\sigma = \frac{PR}{h}$$

where P is the pressure, R is the vessel radius and h is the wall thickness. Intramural stress is therefore directly proportional to the pressure-radius product and inversely proportional to the wall thickness. Consequently, if the pressure-radius product increases by a factor of X, the thickness of the vessel should also increase generally by a factor of X in order to maintain the same level of intramural stress.

Figure 3:
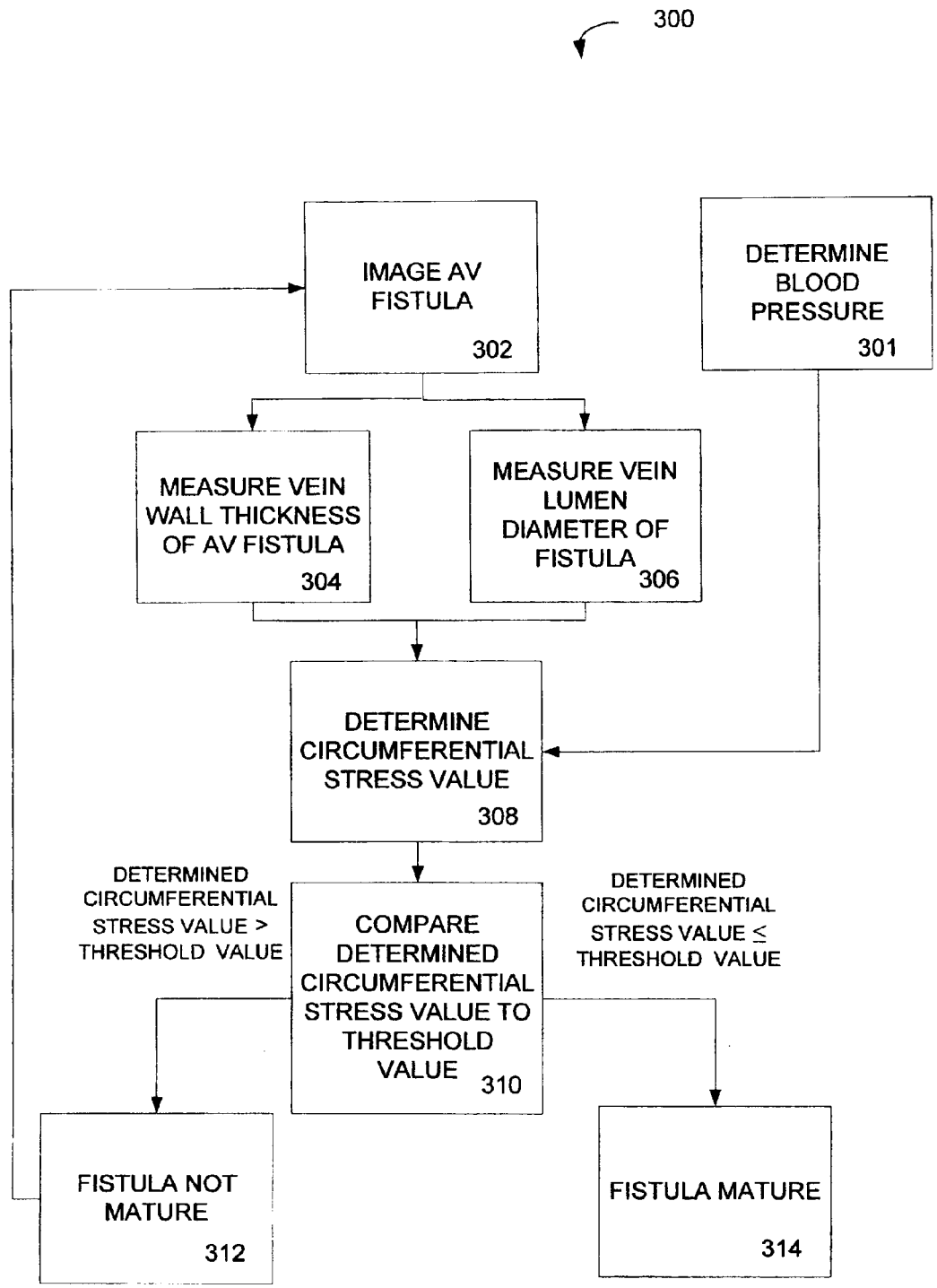
FIG. 3 is a block flow diagram illustrating an exemplary method of detecting a maturing or mature AV fistula in a subject.

Referring now to the embodiment of the present invention illustrated in FIG. 3, further provided herein is a method of detecting a mature arterio-venous fistula comprising a vein, wherein the method comprises determining blood pressure in the subject, as shown in block 301, determining wall thickness of the vein as shown in block 304, and determining a lumen diameter of the vein as shown in block 306 using a high frequency ultrasound imaging system. Blood pressure can be determined by methods known to those skilled in the art. One skilled in the art will readily appreciate that the determined lumen diameter can be used to determine the lumen radius. The determined blood pressure, wall thickness, and lumen radius can be used to determine a circumferential vessel wall stress value σ as shown in block 308. The determined wall stress can be compared to a threshold stress value as shown in block 310. A non-mature arterio-venous fistula is indicated when the determined wall stress is greater than a threshold stress as shown in block 312. A mature arterio-venous fistula is indicated when the determined wall stress is less than or equal to a threshold stress as shown in block 314.

Table 1 shows exemplary calculations of hoop stress (circumferential wall stress) based on exemplary calculations of blood pressure, wall thickness and vessel radius (or diameter).

TABLE 1

| wall thickness is (mm) | MAP × mmHg | radius × (mm) | CF/ | hoop stress N/m2 | diameter (cm) |
|---|---|---|---|---|---|
| 5.54E−02 | 93 | 1.25 | 133.322 | 2.80E+05 | 0.25 |
| 9.74E−02 | 93 | 2.2 | 133.322 | 2.80E+05 | 0.44 |
| 1.11E−01 | 93 | 1.25 | 133.322 | 1.40E+05 | 0.25 |
| 1.95E−01 | 93 | 2.2 | 133.322 | 1.40E+05 | 0.44 |
| 2.21E−01 | 93 | 1.25 | 133.322 | 7.00E+04 | 0.25 |
| 3.90E−01 | 93 | 2.2 | 133.322 | 7.00E+04 | 0.44 |
| 6.73E−02 | 113 | 1.25 | 133.322 | 2.80E+05 | 0.25 |
| 1.18E−01 | 113 | 2.2 | 133.322 | 2.80E+05 | 0.44 |
| 1.35E−01 | 113 | 1.25 | 133.322 | 1.40E+05 | 0.25 |
| 2.37E−01 | 113 | 2.2 | 133.322 | 1.40E+05 | 0.44 |
| 2.69E−01 | 113 | 1.25 | 133.322 | 7.00E+04 | 0.25 |
| 4.73E−01 | 113 | 2.2 | 133.322 | 7.00E+04 | 0.44 |
| 7.50E−02 | 126 | 1.25 | 133.322 | 2.80E+05 | 0.25 |
| 1.32E−01 | 126 | 2.2 | 133.322 | 2.80E+05 | 0.44 |
| 1.50E−01 | 126 | 1.25 | 133.322 | 1.40E+05 | 0.25 |
| 2.64E−01 | 126 | 2.2 | 133.322 | 1.40E+05 | 0.44 |
| 3.00E−01 | 126 | 1.25 | 133.322 | 7.00E+04 | 0.25 |
| 5.28E−01 | 126 | 2.2 | 133.322 | 7.00E+04 | 0.44 |

CF = conversion factor to harmonize the units
vessel diameter range .25-.44 cm
hoop stress range 0.7-2.8E5N/m2
pressure range 93-126 mmHg
wall thickness range 5.54E−2 to 5.28E−1

Table 1 can be used to determine exemplary threshold hoop stress values for use in the described methods. The values in Table 1 for wall thickness, vessel radius (or diameter) and blood pressure are not intended to be limiting. These numbers are exemplary and are provided to demonstrate a range of threshold hoop stress values for comparison to determined values for determining maturation of a fistula as described herein. The determined hoop stress value can be determined for a vessel of a fistula wherein the vessel has any variety of wall thickness and radius (or diameter) characteristics and wherein the subject has any blood pressure value given the equations and description provided herein. Such determined values can be compared to the exemplary threshold hoop stress values or values therebetween provided in Table 1.

In some aspects, a determined hoop stress of between about 2.80E+05 and about 7.00E+04 or less can be used to indicate a mature fistula. Thus, if a determined circumferential stress value is greater than a threshold value of 2.80E+05 then it can be determined that the fistula is not mature. If a determined circumferential stress value is less than or equal to a threshold value of 2.80E+05 then it can be determined that the fistula is mature. In other aspects, a hoop stress of between about 1.40E+05 and 7.00E+04 or less can be used to indicate a mature fistula. Thus, if a determined circumferential stress value is greater than a threshold value of 1.40E+05 then it can be determined that the fistula is not mature. If a determined circumferential stress value is less than or equal to a threshold value of 1.40E+05 then it can be determined that the fistula is mature. In other aspects, a hoop stress of less than about 7.00E+04 can be used to indicate a mature fistula. Thus, if a determined circumferential stress value is greater than a threshold value of 7.00E+04 then it can be determined that the fistula is not mature. If a determined circumferential stress value is less than or equal to a threshold value of 7.00E+04 then it can be determined that the fistula is mature.

In some aspects a determined circumferential vessel stress value can be compared to a predetermined threshold stress value. If the determined circumferential vessel stress is less than or equal to the predetermined threshold stress value then it can be determine that the fistula is mature. If the determined circumferential vessel stress value is greater than the predetermined threshold stress then it can be determined that the fistula is not mature. In these exemplary aspects the predetermined stress value can be between about 7.00E+04 to 2.80E+05. In other exemplary aspects, the predetermined stress value can be between about 7.00E+04 to 1.40E+05. In other exemplary aspects, the predetermined stress can be less than or equal to about 7.00E+04.

In addition to determining whether an arterio-venous fistula is mature, the methods discussed herein can also be used to determine whether an arterio-venous fistula is maturing. Accordingly, a method of detecting a maturing arterio-venous fistula comprising a vein can comprise determining blood pressure in the subject, wall thickness of the vein, and a lumen diameter of the vein using a high frequency ultrasound imaging system. One skilled in the art will readily appreciate that the determined lumen diameter can be used to determine the lumen radius. The determined blood pressure, wall thickness, and lumen radius can be used to determine circumferential vessel wall stress. A maturing arterio-venous fistula is indicated when the determined wall stress is less than or equal to a threshold stress, and a non-maturing arterio-venous fistula is indicated when the determined wall stress is greater than a threshold stress.

Also provided herein is a method for monitoring the maturation of an arterio-venous fistula in a subject wherein the fistula defines a lumen. The method can comprise determining both the vein wall thickness and vein lumen diameter of the fistula using a high frequency ultrasound imaging system. The ratio of vein wall thickness and vein lumen diameter can be compared to a predetermined threshold value, wherein a determined ratio greater than the threshold value indicates a mature arterio-venous fistula. As shown, for example, in Table 1 vein wall thickness and radius (or diameter) can vary. The predetermined threshold value can be determined by determining the ratio at which the fistula fails.

When measuring the maturity level of a fistula using any of the disclosed methods, the methods can further comprise measuring the blood flow velocity associated with the fistula. Blood flow velocity can be used to estimate the blood pressure within a fistula.

Optionally, the velocity of blood flow can be measured upstream from the fistula, downstream from the fistula, and/or within the fistula. Known methods of ultrasonic blood flow velocity measurement can be used. For example, Doppler ultrasound imaging methods and modes can be used to measure the velocity of blood flow associated with a fistula. The velocity can be analyzed along with the measurements on vein wall thickness to determine the maturity of the fistula or whether the fistula is maturing. The Doppler measurements can be taken with the same high frequency ultrasound system used to produce the vein wall thickness measurements. Alternatively, a separate, high or clinical frequency ultrasound system could be used to produce blood flow velocity measurements.

Also in conjunction with the methods of measuring vein wall thickness, an ultrasound contrast agent can be delivered to the lumen of the fistula and imaging the fistula comprising ultrasound contrast agent can be performed. Images of the fistula comprising contrast agent can be used with the measurements of wall thickness and/or blood flow velocity to determine the maturity of the fistula or whether the fistula is maturing.

A contrast agent for use in the disclosed methods can comprise a thin flexible or rigid shell composed of albumin, lipid or polymer confining a gas such as nitrogen or a perflurocarbon. Other examples of representative gases include air, oxygen, carbon dioxide, hydrogen, nitrous oxide, inert gases, sulfur fluorides, hydrocarbons, and halogenated hydrocarbons, perfluorobutane, perfluoropropane, and sulfur hexafluoride. Liposomes or other microbubbles can also be designed to encapsulate gas or a substance capable of forming gas.

Administration of contrast imaging agents can be carried out in various fashions using a variety of dosage forms. One preferred route of administration is intravascularly. For intravascular use, the contrast agent can be injected intravenously, but can be injected intra-arterially as well. The useful dosage to be administered and the mode of administration can vary depending upon the age and weight of the subject, and on the particular diagnostic application intended. In one aspect, a dosage can be initiated at lower levels and increased until the desired contrast enhancement is achieved. A contrast agent can be administered in the form of an aqueous suspension such as in water or a saline solution (e.g., phosphate buffered saline). In this aspect, the water can be sterile and the saline solution can be a hypertonic saline solution (e.g., about 0.3 to about 0.5% NaCl), although, if desired, the saline solution can be isotonic. Optionally, the solution also can be buffered, if desired, to provide a pH range of pH 6.8 to pH 7.4. In addition, dextrose can be included in the media.

Further provided is a method comprising measuring the thickness of the vein wall at multiple locations and determining a level of statistical variation in thickness along a length of the vein. Measured statistical variation can be used to determine the maturity of a fistula or whether a fistula is maturing. For example, a lower level of statistical variation in the thickness of the vein as compared to the level of statistical variation in the thickness of the vein calculated at a prior time can indicate a maturing fistula and/or a mature fistula.

An exemplary ultrasound system can comprise software for producing an ultrasound image, for taking wall measurements, for comparing wall measurements, and for analyzing blood flow velocity. Such software can comprise an ordered listing of executable instructions for implementing logical functions, and can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

For example, the control value can be stored in the ultrasound system in a computer readable code or medium or can be similarly stored in a separate computational device. Software of the ultrasound system or computational device can compare the measured wall thickness to a control value and can determine whether wall thickening, fistula maturation, or a mature fistula is present. Thus, the system can comprise computer readable code and a processor for determining a vein wall thickness from the image captured at an initial time and from the image captured at a subsequent time. The system can also comprise computer readable code and a processor for comparing the initial wall thickness determined from an initial image to the subsequent wall thickness determined from a subsequent image, wherein an increased subsequent wall thickness as compared to the initial wall thickness indicates wall thickening of the vein.

In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM), a read-only memory (ROM), an erasable programmable read-only memory (EPROM or Flash memory) (magnetic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

An exemplary imaging system can include memory. Memory can include the image data obtained by an ultrasound system. A computer readable storage medium can be coupled to the processor for providing instructions to the processor to instruct and/or configure processor to perform steps or algorithms related to the operation of the ultrasound system, including algorithms related to the measurement of a vein wall or to analysis of blood flow velocity.

The computer readable medium can include hardware and/or software such as, by way of example only, magnetic disks, magnetic tape, optically readable medium such as a CD ROM, and semiconductor memory such as a PCMCIA card. In each case, the medium may take the form of a portable item such as a small disk, floppy diskette, cassette, or it may take the form of a relatively large or immobile item such as hard disk drive, solid state memory card, or RAM provided in the support system. It should be noted that the above listed example mediums can be used either alone or in combination.

EXAMPLES

The following examples are put forth so as to provide those of ordinary skill in the art with a complete disclosure and description of how the compositions, articles, devices, systems, and/or methods claimed herein are made and evaluated, and are intended to be purely exemplary and are not intended to limit the scope of compositions, compositions, articles, devices, systems, and/or methods. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Figure 4:
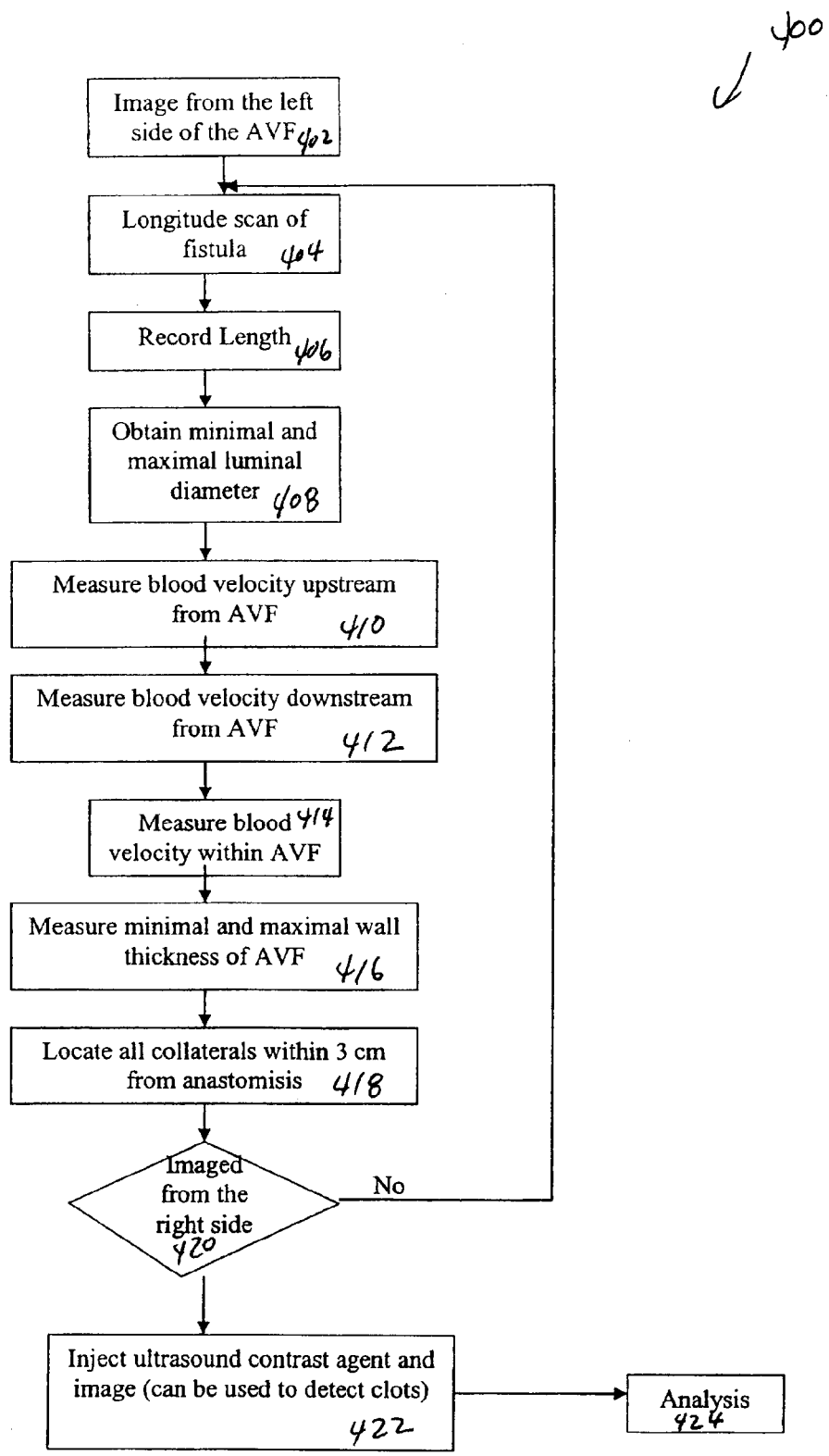
FIG. 4 is a block flow diagram illustrating an exemplary method of detecting a maturing AV fistula in a subject.

An exemplary process 400 for analyzing an arterio-venous fistula is shown in FIG. 4. A fistula is longitudinally scanned from the left side and an approximate length is recorded as shown in blocks 402, 404 and 406 respectively. The ultrasound beam is directed perpendicular to the near wall. The minimal luminal diameter and maximal luminal diameter is obtained as shown in block 408. Blood velocity is measured by pulsed Doppler upstream from AVF (arterial end) as shown in block 410. Blood velocity is measured by pulsed Doppler downstream from AVF (venous end) as shown in block 412. Blood velocity is measured by pulsed Doppler within the AVF as shown in block 414. The maximal wall thickness of AVF is measured and the minimal wall thickness of AVF is measured as shown in block 416. Collateral veins within approximately 3.0 cm from the anastomosis are identified as shown in block 418. The process steps can be repeated with an image created from the right side of the fistula as shown in block 420. Ultrasound contrast agent for AVF luminal enhancement and targeted ultrasound contrast agent targeted to a clot antigen can be used to better delineate AVF stenosis or AVF failure and the causes thereof can be injected as shown in block 422. The analysis shown in block 424 can comprise determining if the fistula is maturing, is mature or if a wall of the vein in the fistula has thickened.

Example 2

Figure 5:
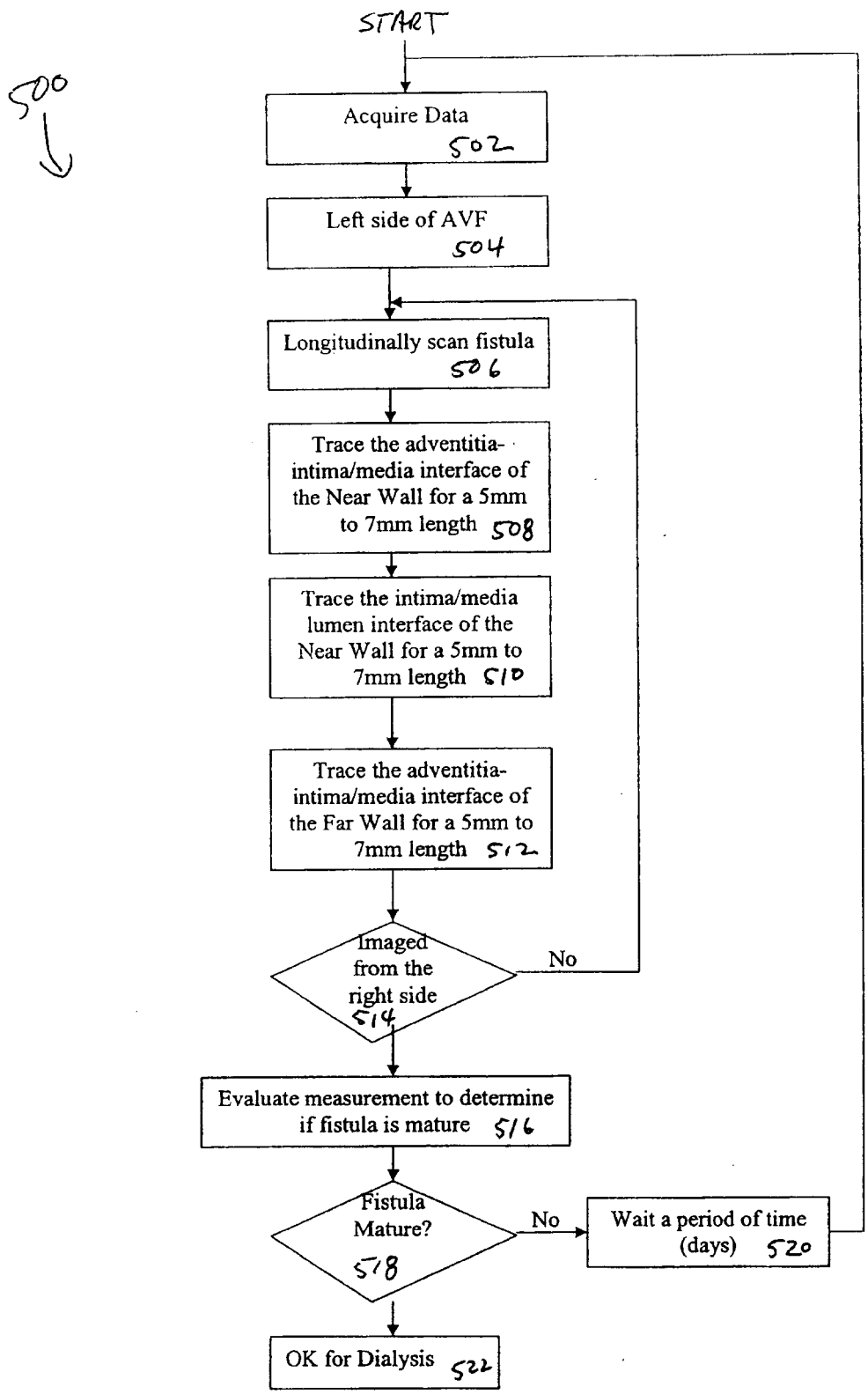
FIG. 5 is a block flow diagram illustrating an exemplary method of detecting a maturing AV fistula in a subject.
Figure 6:
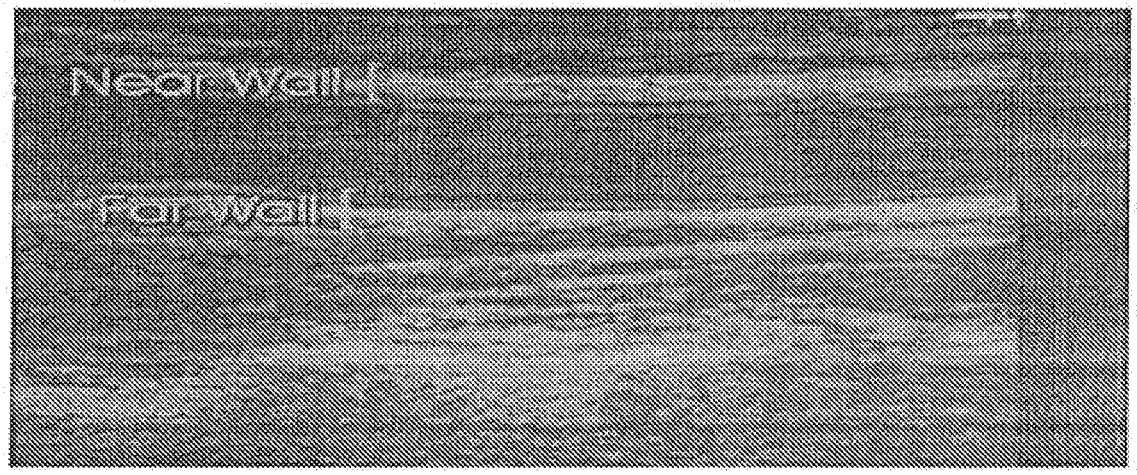
FIG. 6 is a longitudinal ultrasonic image of a fistula comprising a vein.
Figure 7:
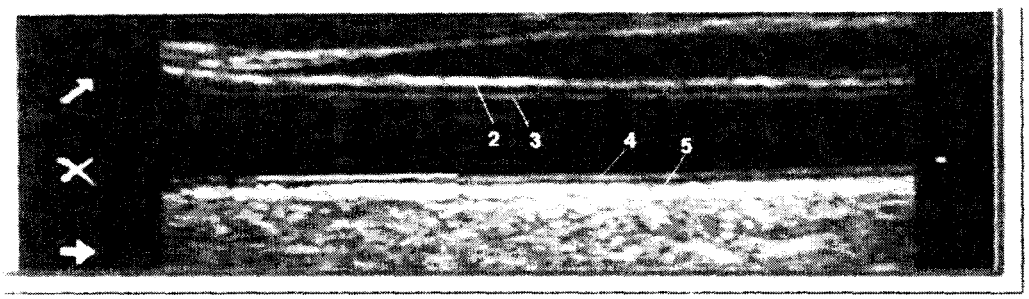
FIG. 7 is a longitudinal ultrasonic image of a fistula comprising a vein.

A second exemplary process 500 for analyzing an arterio-venous fistula is shown in FIG. 5. A longitudinal ultrasound image of the AVF is captured from the left side as shown in blocks 502, 504, and 506. Measurements from the images on the left side views of the AVF are performed. On the near wall of the AVF a caliper is placed on the bottom of the adventitia (the bottom of the first bright reflection line) and the interface is traced for a 5-7 mm length segment as shown in block 508 and in FIG. 6. A second caliper is placed at the interface where the intima/media meets the lumen (the bottom of the second bright reflection line) and this interface is traced for the same 5-7 mm length as shown in block 518 and in FIG. 6. On the far wall of the AVF a third caliper is placed at the interface where the lumen meets the intima/media (the top the first bright reflection line) and this segment is traced for the same 5-7 mm length as shown in block 512 and in FIG. 6. A fourth caliper is placed at the interface where the intima/media meets the adventitia (top of the second bright reflection line) and this interface is traced for the same 5-7 mm length as shown in block 512 and in FIG. 6. The placing of the calipers and measurements can be repeated on the image taken of the right side of the AVF as shown in block 514. The measurements can be repeated at multiple positions along the fistula as shown in FIG. 7. For example, as shown in FIG. 7, the adventitia-intima/media interface can be identified at point 2 and the intima/media-lumen interface can be identified at point 3 both on the near wall. Similarly, on the far wall, the lumen-intima/media interface can be identified at point 4 and the intima/media-adventitia interface can be identified at point 5. The thickness of the near wall can be determined by measuring the distance between points 2 and 3, and the thickness of the far wall can be determined by measuring the distance between points 4 and 5. The measurements can be evaluated to determine if the fistula is maturing or if the fistula is mature. If the fistula is mature, the vein can be accessed for dialysis. If the fistula is not mature, the process steps can be repeated after a period of time has passed to allow for further maturation.

The preceding description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. The corresponding structures, materials, acts, and equivalents of all means or step plus function elements in the claims below are intended to include any structure, material, or acts for performing the functions in combination with other claimed elements as specifically claimed.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification. The blocks in the flow charts described above can be executed in the order shown, out of the order shown, or substantially in parallel.

Accordingly, those who work in the art will recognize that many modifications and adaptations to the present invention are possible and can even be desirable in certain circumstances and are a part of the present invention. Other embodiments of the invention will be apparent to those skilled in the art from consideration of the specification and practice of the invention disclosed herein. Thus, the preceding description is provided as illustrative of the principles of the present invention and not in limitation thereof. It is intended that the specification and examples be considered as exemplary only, with a true scope and spirit of the invention being indicated by the following claims.

What is claimed is:

1. A method for operating an ultrasound system to detect maturation of an arterio-venous fistula in a subject, the arterio-venous fistula defining a lumen, comprising:
    transmitting ultrasound pulses into the subject from a transducer coupled to the ultrasound system;
    receiving ultrasound echoes at the transducer;
    constructing an ultrasound image of the fistula using data acquired from the received ultrasound echoes;
    calculating a wall thickness of the arterio-venous fistula based on a first distance between a first point in the ultrasound image corresponding to a first location on an outer wall of the arterio-venous fistula and a second point in the ultrasound image corresponding to a second location on an inner surface of the lumen;
    calculating a diameter or radius of the lumen of the arterio-venous fistula based on a second distance between third and fourth points in the ultrasound image corresponding to third and fourth locations, respectively, on the inner surface of the lumen, wherein the third point is diametrically opposed to the fourth point;
    calculating a circumferential stress based on the wall thickness and the diameter or radius of the lumen;
    comparing the circumferential stress to a predetermined threshold wherein the predetermined threshold is between about 7.00E+04 to 2.80E+05 N/m$^2$; and
    producing a notification that the arterio-venous fistula is mature if the calculated circumferential stress is less than or equal to the predetermined threshold.

2. The method of claim 1, further comprising measuring a blood pressure of the subject.

3. The method of claim 2, wherein determining the circumferential stress comprises determining the circumferential stress of the arterio-venous fistula from the wall thickness, the diameter or radius of the lumen, and the blood pressure.

4. The method of claim 3, wherein the circumferential stress of the arterio-venous fistula is determined by the following:

$$\sigma = \frac{PR}{h}$$

where $\sigma$ is the circumferential stress, P is the blood pressure, R is the radius of the lumen and h is the wall thickness.

5. The method of claim 1, further comprising determining if the determined circumferential stress is less than or equal to the predetermined threshold.

6. The method of claim 1, further comprising determining if the circumferential stress is greater than the predetermined threshold.

7. The method of claim 1, further comprising notifying an operator that the arterio-venous fistula is not mature.

8. The method of claim 1, wherein the predetermined threshold is between about 7.00E+04 to 1.40E+05 N/m$^2$.

9. The method of claim 1, wherein the predetermined threshold is less than or equal to about 7.00E+04 N/m$^2$.

10. The method of claim 1 wherein the second location is the same as the third location or the fourth location.

11. A method for operating an ultrasound system to detect a maturation of an arterio-venous fistula in a subject, the arterio-venous fistula defining a lumen, comprising:
    transmitting ultrasound pulses into the subject from a transducer coupled to the ultrasound system;
    receiving ultrasound echoes at the transducer;
    constructing an ultrasound image of the arterio-venous fistula using data acquired from the received ultrasound echoes;
    calculating a wall thickness of the arterio-venous fistula based on a first distance between a first point in the ultrasound image corresponding to a first location on an outer wall of the fistula and a second point in the ultrasound image corresponding to a second location on an inner surface of the lumen;
    calculating a lumen diameter of the arterio-venous fistula based on a second distance between third and fourth points in the ultrasound image corresponding to third and fourth locations, respectively, on the inner surface of the lumen, wherein the third point is diametrically opposed to the fourth point; and
    comparing a ratio of the wall thickness and the lumen diameter to a predetermined threshold, wherein the predetermined threshold is less than or equal to about 2.80E+05 N/m$^2$; and
    producing a notification that the arterio-venous fistula is mature if a value of the ratio is less than the predetermined threshold.

12. The method of claim 11 further comprising measuring a blood flow velocity associated with the arterio-venous fistula using a Doppler ultrasound imaging system.

13. The method of claim 11, further comprising analyzing the blood flow velocity in conjunction with the wall thickness and the lumen diameter.

14. The method of claim 9 wherein the second location is the same as the third location or the fourth location.

15. A system for operating an ultrasound system to detect a maturation of an arterio-venous fistula in a subject, the arterio-venous fistula defining a lumen, comprising:
    a high frequency ultrasound imaging system having a center frequency of at least 10 (megahertz) MHz;
    means for measuring a wall thickness of the arterio-venous fistula using the high frequency ultrasound imaging system;
    means for measuring a diameter of the lumen of the arterio-venous fistula using the high frequency ultrasound imaging system;
    a processor;
    means for transmitting measurements of the wall thickness and diameter of the lumen to the processor,
        wherein the processor is configured to determine a circumferential stress for the arterio-venous fistula based on at least one of the wall thickness, the diameter of the lumen, and a blood pressure of the subject, and
        wherein the processor is configured to compare the circumferential stress to a predetermined threshold, wherein the predetermined threshold is between about 7.00E+04 to 2.80E+05 N/m$^2$; and
    means for outputting a notification to an operator that the arterio-venous fistula is mature if the circumferential stress is less than or equal to the predetermined threshold.

16. The system of claim 15, wherein the processor determines if the circumferential stress is greater than the predetermined threshold and outputs a notification to an operator that the arterio-venous fistula is not mature.

17. The system of claim 15, wherein the predetermined threshold is between about 7.00E+04 to 1.40E+05 N/m$^2$.

18. The system of claim 15, wherein the predetermined threshold is less than or equal to about 7.00E+04 N/m$^2$.

* * * * *

UNITED STATES PATENT AND TRADEMARK OFFICE
CERTIFICATE OF CORRECTION

| | |
|---|---|
| PATENT NO. | : 8,529,452 B2 |
| APPLICATION NO. | : 12/303137 |
| DATED | : September 10, 2013 |
| INVENTOR(S) | : Donnelly et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 979 days.

Signed and Sealed this
Twenty-fourth Day of February, 2015

Michelle K. Lee
*Deputy Director of the United States Patent and Trademark Office*